(12) United States Patent
Wang et al.

(10) Patent No.: US 10,743,028 B2
(45) Date of Patent: Aug. 11, 2020

(54) MULTIPLE SIGN BIT HIDING WITHIN A TRANSFORM UNIT

(71) Applicant: VELOS MEDIA, LLC, Plano, TX (US)

(72) Inventors: Jing Wang, Waterloo (CA); Xiang Yu, Kitchener (CA); Dake He, Waterloo (CA)

(73) Assignee: Velos Media, LLC, Dallas, TX (US)

( * ) Notice: Subject to any disclaimer, the term of this patent is extended or adjusted under 35 U.S.C. 154(b) by 0 days.

(21) Appl. No.: 15/894,085

(22) Filed: Feb. 12, 2018

(65) Prior Publication Data

US 2018/0167635 A1 Jun. 14, 2018

Related U.S. Application Data

(63) Continuation of application No. 14/682,462, filed on Apr. 9, 2015, now Pat. No. 9,900,622, which is a
(Continued)

(51) Int. Cl.
*H04N 19/625* (2014.01)
*H04N 19/129* (2014.01)
(Continued)

(52) U.S. Cl.
CPC ........... *H04N 19/625* (2014.11); *H04N 11/02* (2013.01); *H04N 11/04* (2013.01); *H04N 19/129* (2014.11);
(Continued)

(58) Field of Classification Search
CPC ........... G01B 9/06; G01P 13/00; G01P 15/00; G01C 21/02; G01S 17/66; H04N 7/26372;
(Continued)

(56) References Cited

U.S. PATENT DOCUMENTS

| 4,463,377 A | 7/1984 | Meyer-Ebrecht |
| 4,807,033 A | 2/1989 | Keesen |

(Continued)

FOREIGN PATENT DOCUMENTS

| CN | 1383684 | 4/2002 |
| CN | 101185083 | 5/2008 |
| WO | 2007025476 | 3/2007 |

OTHER PUBLICATIONS

"Data Hiding of Intra Prediction Information in Chroma Samples for Video Compression" by J-M. Thiesse, J. Jung, and M. Antonini, 978-1-4244-7993-1 (c)2010 IEEE (Year: 2010).*
(Continued)

*Primary Examiner* — Dramos Kalapodas
(74) *Attorney, Agent, or Firm* — Spencer C. Patterson; Grable Martin Fulton PLLC

(57) ABSTRACT

Methods of encoding and decoding for video data are described for encoding or decoding coefficients for a transform unit. In particular, the sign bits for the non-zero coefficients are encoded using sign bit hiding. Two or more sets of coefficients are defined for the transform unit and a sign bit may be hidden for each set, subject to satisfaction of a threshold test. The sets may correspond to coefficient groups that are otherwise used in multi-level significance map encoding and decoding.

13 Claims, 11 Drawing Sheets

Related U.S. Application Data continuation of application No. 13/354,465, filed on Jan. 20, 2012, now Pat. No. 9,008,184.

(51) Int. Cl.

| | |
|---|---|
| *H04N 19/176* | (2014.01) |
| *H04N 19/51* | (2014.01) |
| *H04N 11/02* | (2006.01) |
| *H04N 11/04* | (2006.01) |
| *H04N 19/40* | (2014.01) |
| *H04N 19/593* | (2014.01) |

(52) U.S. Cl.
CPC ........... *H04N 19/176* (2014.11); *H04N 19/40* (2014.11); *H04N 19/51* (2014.11); *H04N 19/593* (2014.11)

(58) Field of Classification Search
CPC ....... H04N 19/00781; H04N 19/00278; H04N 19/00296; H04N 19/00303; H04N 19/00157; H04N 19/00121; H04N 19/00109; H04N 19/00684; H04N 19/00696; H04N 19/48; H04N 19/467; H04N 7/30; H03M 7/4006
See application file for complete search history.

(56) References Cited

U.S. PATENT DOCUMENTS

| | | | |
|---|---|---|---|
| 5,218,650 A | | 6/1993 | Blonstein |
| 5,295,203 A * | | 3/1994 | Krause ................ G06T 9/008 |
| | | | 382/248 |
| 5,481,553 A * | | 1/1996 | Suzuki ................ G06F 17/147 |
| | | | 375/240.15 |
| 5,590,139 A * | | 12/1996 | Suzuki ................ G06F 17/147 |
| | | | 714/800 |
| 5,909,249 A | | 6/1999 | Sathe et al. |
| 6,757,437 B1 | | 6/2004 | Keith et al. |
| 7,190,840 B2 | | 3/2007 | Said |
| 7,738,558 B2 | | 6/2010 | Ma |
| 2005/0129271 A1* | | 6/2005 | Shi ....................... G06T 1/0028 |
| | | | 382/100 |
| 2009/0003098 A1* | | 1/2009 | Hoess .................. G11C 29/832 |
| | | | 365/200 |
| 2009/0097571 A1 | | 4/2009 | Yamada et al. |
| 2009/0122868 A1* | | 5/2009 | Chen ..................... H03M 7/30 |
| | | | 375/240.22 |
| 2009/0254759 A1 | | 10/2009 | Michiels et al. |
| 2010/0208804 A1* | | 8/2010 | Yu ..................... H04N 21/2383 |
| | | | 375/240.12 |
| 2010/0208805 A1* | | 8/2010 | Yu ....................... H04N 19/147 |
| | | | 375/240.12 |
| 2010/0208806 A1* | | 8/2010 | Yu ....................... H04N 19/176 |
| | | | 375/240.12 |
| 2010/0211857 A1 | | 8/2010 | Kobayashi |
| 2010/0220783 A1 | | 9/2010 | Mallat et al. |
| 2011/0268183 A1* | | 11/2011 | Sole ..................... H04N 19/70 |
| | | | 375/240.03 |
| 2011/0310974 A1 | | 12/2011 | Shand |
| 2012/0163448 A1 | | 6/2012 | Zheng et al. |
| 2013/0051459 A1 | | 2/2013 | Kirchhoffer |
| 2013/0114730 A1 | | 5/2013 | Joshi |
| 2014/0301462 A1 | | 10/2014 | Gu |

OTHER PUBLICATIONS

Thomas Davies (hereinafter Davies) "Unified Scan Processing for High Efficiency Coefficient Coding", JCTVC-D219, 4th Meeting: Daegu, KR Jan. 20-28, 2011: WG11 No. m18979 (Year: 2011).*
Gordon Clare et al., (hereinafter Clare) "Sign Data Hiding" JCTVC-G271; 7th Meeting: Geneva, CH, Nov. 21-30, 2011 (Year: 2011).*
Thomas Davies "Unified Scan Processing for High Efficiency Coefficient Coding", JCTVC-D219, 4th Meeting: Daegu, KR Jan. 20-28, 2011: WG11 No. m18979 (Year: 2011).*
Gordon Clare et al., "Sign Data Hiding" JCTVC-G271; 7th Meeting: Geneva, CH, Nov. 21-30, 2011 (Year: 2011).*
Nguyen et al..: "Multi-level Significant Maps for Large Transform Units", 7. JCT-VC Meeting; 98. MPEG Meeting; Nov. 21, 2011-Nov. 30, 2011; Geneva; (Joint Collaborative Team on Video Coding of ISO/IEC JTC1/SC29?WG11 and ITU-T SG. 16 (Year: 2011).*
Thiesse et al.: "Data hiding of motion information in chroma and luma samples for video compression", 2010 IEEE International Workshop on Multimedia Signal Processing (MMSP '10), Saint Malo, France, Oct. 4-6, 2010, IEEE, Piscataway, USA, Oct. 4, 2010, pp. 217-221, XP031830585 (Year: 2010).*
Marpe, H. Schwarz, and T. Wiegand, "Context-based adaptive binary arithmetic coding in the h.264/AVC video compression standard," IEEE Transactions on Circuits and Systems for Video Technology, 13(7):620-636, Jul. 2003.
B. Bross, W-J Han, J-R Ohm, G. J. Sullivan, and T. Wiegand, "WD4: Working Draft 4 of High-Efficiency Video Coding," JCT-VC of ITU-T SG16 WP3 and ISO/IEC JTC1/SC29/WG11, 6th Meeting, Torino, Jul. 2011.
F. Bossen, "Common test conditions and software reference configurations", JCTVC-F900, JCT-VC of ITU-T SG16 WP3 and ISO/IEC JTC1/SC29/WG11, 6th Meeting, Torino, Jul. 2011.
T. Nguyen, T. Winken, D. Marpe et al., "Reduced-complexity entropy coding of transform coefficient levels using a combination of VLC and PIPE", JCTVC-D336, JCT-VC of ITU-T SG16 WP3 and ISO/IEC JTC1/SC29/WG11, 4th Meeting, Daegu, Jan. 2011.
"Entropy Coding of Syntax Elements Related to Block Structures and Transform Coefficient Levels in HEVC", by Tung Nguyen et al., School of EE & CS, Berlin Institute of Technology, Germany, 2012.
J. Sole, R. Joshi, M. Marczewicz, "Non-CE11: Diagonal sub-block scan for HE residual coding", JCTVC-G323.
N. Nguyen, T. Ji, D. He, G. Martin-Cocher, L. Song, "Multi-level significance maps for large transform units", JCTVC-G644.
Benjamin Bross, et al. "WD5: Working Draft 5 of High-Efficiency Video Coding" JCTVC-G1103_d4.
EPO, Extended European Search Report relating to application No. 12151973.0 dated Jul. 9, 2012.
Clare (Orange Labs) G et al., "Sign Data Hiding", 7, JCT-VC Meeting; 98; MPEG Meeting; Nov. 21, 2011-Nov. 30, 2011; Geneva; (Joint Collaborative Team on Video Coding of ISO/IEC JTC1/SC29/WG11 and ITU-T SG. 16); URL: http://wftp3.itu.int/av-arch/jctvc-site/,, No. JCTVC-G271, Nov. 8, 2011, XP030110255.
Amonou (FT) I et al., "Description of Video Coding Technology Proposal by France Telecom, NTT, NTT DOCOMO, Panasonic and Technicolor", 1. JCT-VC Meeting; Apr. 15, 2010-Apr. 23, 2010; Dresden; (Joint Collaborative Team on Video Coding of ISO/IEC JTC1/SC29/WG11 and ITU-T SG.16); URL: http://wftp3; itu.int/av-arch/jctvc-site/,, No. JCTVC-A114, Apr. 13, 2010, XP030009031.
J-M Thiesse et al: "Data Hiding of Intra Prediction Information in Chroma Samples for Video Compression", 2010 17th IEEE International Conference on Image Processing: (ICIP 2010); Hong Kong, Sep. 26-29, 2010, IEEE, Piscataway, NJ, USA, Sep. 26, 2010, XP031813491.
EPO Examination Report dated Oct. 24, 2013.
Nguyen et al.: "Multi-level Significant Maps for Large Transform Units", dated Nov. 30, 2011, XP030110628.
Australian Patent Office, AU Office Action relating to Application No. 2013200325, dated Nov. 12, 2013.
"Transform Coding in the HEVC Test Model", by Martin Winken et al., 978-1-4577-13-3-3/11© IEEE 2011.
"Data Hiding in Encoded Video Sequences Based on H.264", by Xiaoni Li et al., 978-1-4224-5539-3/10© 2010, IEEE.
Japanese Patent Office, JP Office Action relating to Application No. 2013-6987, dated Nov. 7, 2013.
Miyake et al.: "A Steganography for JPEG Bitstreams", Computer Security Symposium 2002, Information Processing Society of Japan dated Oct. 30, 2002, ISSN: 1344-0640.
"Reversible Data Hiding-Based Approach for Intra-Frame Error Concealment in H.264/QVC" by Kuo-Liang et al.,© 2010 IEEE.

(56) References Cited

OTHER PUBLICATIONS

Notices of Reasons for Rejection, Shusaku Yamamoto, Patent Application No. 2013-006987.
Davies: "Unified scan processing for high efficiency coefficient coding", Joint Collaborative Team on Video Coding (JCT-VC) of ITU-T SG16 WP3 and ISO/IEC JTC1/SC29/WG11, 4th Meeting: Daegu, KR, Jan. 20-28, 2011, Document: JCTVC-D219.
Clare et al.: "Sign Data Hiding", Joint Collaborative Team on Video Coding (JCT-VC), of ITU-T SG16 WP3 and ISO/IEC JTC1/SC29/WG11, 7th Meeting: Geneva, CH, Nov. 21-30, 2011, Document: JCTVC-G271.
EPO, Extended European Search Report relating to EP application No. 16176581.3, dated Oct. 11, 2016.
Clare et al.: "Sign Data Hiding" 7. JCT-VC Meeting; 98. MPEG Meeting; Nov. 21, 2011-Nov. 30, 2011; Geneva; (Joint Collaborative Team on Video Coding of ISO/IEC JTC1/SC29/WG11 and ITU-T SG.16); No. JCTVC-G271; Nov. 8, 2011, XP030110255.
Nguyen et al.: "Multi-level Significant Maps for Large Transform Units", 7. JCT-VC Meeting; 98. MPEG Meeting Nov. 21, 2011-Nov. 30, 2011; Geneva; (Joint Collaborative Team on Video Coding of ISO/IEC JTC1/SC29/WG11 and ITU-T SG.16); No. JCTVC-G644, Nov. 9, 2011, XP030110628.
U.S. Office Action dated Mar. 2, 2017.
U.S. Office Action dated Aug. 7, 2017.
U.S. Notice of Allowance dated Oct. 11, 2017.
IPO, IN Examination Report relating to IP application No. 133/Che/2013, dated Jul. 11, 2018.
SIPO, CN Office Action relating to CN application No. 201610370914.6, dated Aug. 22, 2018.
EPO Extended European Search Report relating to EP application No. 18159781.6, dated Oct. 1, 2018.
Clare et al.: "Sign data Hiding", 7. JCT-VC Meeting; 98. MPEG Meeting Nov. 21, 2011-Nov. 30, 2011; Geneva; (Joint Collaborative Team on Video Coding of ISO/IEC JTC1/SC29/WG11 and ITU-T SG.16); URL: http://wftp3.itu.int/av-arch/jctvc-site/, No. JCTVC-G271, Nov. 8, 2011, XP030110255.
Nguyen et al..: "Multi-level Significant Maps for Large Transform Units", 7. JCT-VC Meeting; 98. MPEG Meeting; Nov. 21, 2011-Nov. 30, 2011; Geneva; (Joint Collaborative Team on Video Coding of ISO/IEC JTC1/SC29/WG11 and ITU-T SG. 16); URL: http://wftp3.itu.int/av-arch/jctvc-site/, No. JCTVC-G644, Nov. 9, 2011, XP030110628.
Thiesse et al.: "Data hiding of motion information in chroma and luma samples for video compression", 2010 IEEE International Workshop on Multimedia Signal Processing (MMSP '10), Saint Malo, France, Oct. 4-6, 2010, IEEE, Piscataway, USA, Oct. 4, 2010, pp. 217-221, XP031830585.
He et al.: "A Robust Wavelet-Domain Watermarking Algorithm for Color Image", Machine Learning and Cybernetics, 2006 International Conference ON, IEEE, Piscataway, NJ, USA, Aug. 13, 2006, pp. 3940-3943, XP031439912.

* cited by examiner ated as U.S. Pat. No. 9,008,184, the
MULTIPLE SIGN BIT HIDING WITHIN A TRANSFORM UNIT

CROSS-REFERENCE TO RELATED APPLICATIONS

The present application is a continuation of U.S. patent application Ser. No. 14/682,462, filed Apr. 9, 2015 and granted as U.S. Pat. No. 9,900,622, which was a continuation of U.S. patent application Ser. No. 13/354,465, filed Jan. 20, 2012 and granted as U.S. Pat. No. 9,008,184, the contents of both of which are hereby incorporated by reference.

FIELD

The present application generally relates to data compression and, in particular, to methods and devices for sign bit hiding when encoding and decoding residual video data.

BACKGROUND

Data compression occurs in a number of contexts. It is very commonly used in communications and computer networking to store, transmit, and reproduce information efficiently. It finds particular application in the encoding of images, audio and video. Video presents a significant challenge to data compression because of the large amount of data required for each video frame and the speed with which encoding and decoding often needs to occur. The current state-of-the-art for video encoding is the ITU-T H.264/AVC video coding standard. It defines a number of different profiles for different applications, including the Main profile, Baseline profile and others. A next-generation video encoding standard is currently under development through a joint initiative of MPEG-ITU termed High Efficiency Video Coding (HEVC). The initiative may eventually result in a video-coding standard commonly referred to as MPEG-H.

There are a number of standards for encoding/decoding images and videos, including H.264, that use block-based coding processes. In these processes, the image or frame is divided into blocks, typically 4×4 or 8×8, and the blocks are spectrally transformed into coefficients, quantized, and entropy encoded. In many cases, the data being transformed is not the actual pixel data, but is residual data following a prediction operation. Predictions can be intra-frame, i.e. block-to-block within the frame/image, or inter-frame, i.e. between frames (also called motion prediction). It is expected that MPEG-H will also have these features.

When spectrally transforming residual data, many of these standards prescribe the use of a discrete cosine transform (DCT) or some variant thereon. The resulting DCT coefficients are then quantized using a quantizer to produce quantized transform domain coefficients, or indices.

The block or matrix of quantized transform domain coefficients (sometimes referred to as a "transform unit") is then entropy encoded using a particular context model. In H.264/AVC and in the current development work for MPEG-H, the quantized transform coefficients are encoded by (a) encoding a last significant coefficient position indicating the location of the last non-zero coefficient in the transform unit, (b) encoding a significance map indicating the positions in the transform unit (other than the last significant coefficient position) that contain non-zero coefficients, (c) encoding the magnitudes of the non-zero coefficients, and (d) encoding the signs of the non-zero coefficients. This encoding of the quantized transform coefficients often occupies 30-80% of the encoded data in the bitstream.

Transform units are typically N×N. Common sizes include 4×4, 8×8, 16×16, and 32×32, although other sizes are possible, including non-square sizes in some embodiments, such as 8×32 or 32×8. The sign of each non-zero coefficient in a block is encoded using one sign bit for each non-zero coefficient.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

Figure 1:
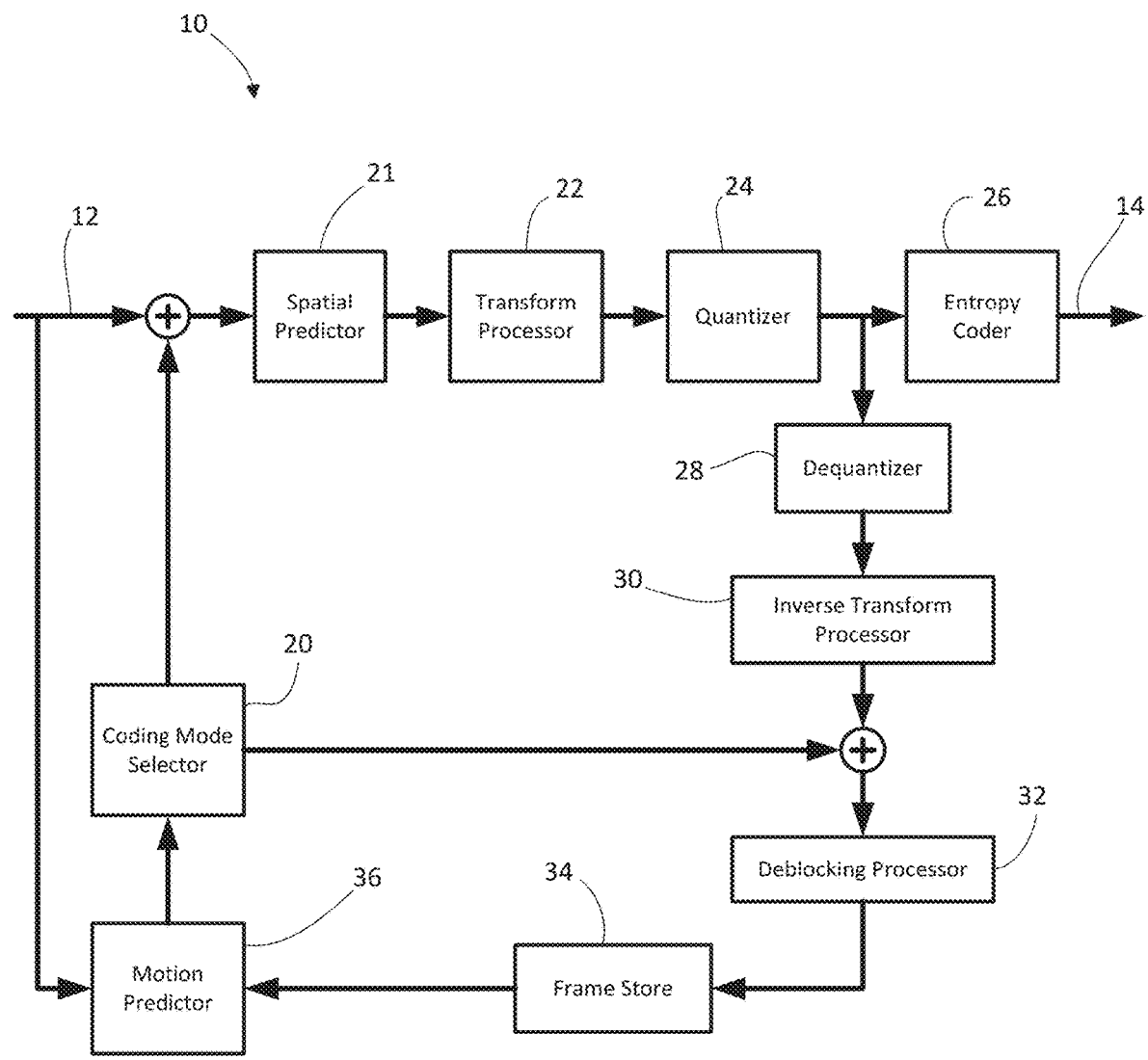
FIG. 1 shows, in block diagram form, an encoder for encoding video.

The present application describes methods and encoders/decoders for encoding and decoding residual video data using sign bit hiding. In some of the embodiments, the encoder and decoder may use multi-level significance maps for encoding significant-coefficient flags. A sign bit of at least one coefficient for each subset of the coefficients in the transform unit may be hidden using a parity technique. In some cases, the subsets of coefficients correspond to the coefficient groups used in the multi-level maps used, for example, in significance map encoding and decoding. In at least one case, the multi-level maps are used with larger transform units, such as the 16×16 and 32×32 TUs. In some cases, multi-level maps are used with 8×8 TUs, non-square TUs, and other size TUs. The sign bit hiding technique may be used for those subsets of coefficients that contain more than a threshold number of non-zero coefficients. In some embodiments, the subset-based sign bit hiding technique may also be used with TUs even if they do not use multi-level significance map encoding, particularly if the significant-coefficient encoding of the TU is modularly implemented for subsets of the significant-coefficient flags.

In one aspect, the present application describes a method of decoding a bitstream of encoded video by reconstructing coefficients for a transform unit, the bitstream encoding two or more sets of sign bits for the transform unit, each set corresponding to a respective non-overlapping set of coefficients for the transform unit, wherein each sign bit indicates the sign of a corresponding non-zero coefficient within the respective set. The method includes, for each of the two or more sets of sign bits, summing an absolute value of the coefficients for the respective set corresponding to that set of sign bits to obtain a parity value; and assigning a sign to one of the coefficients within the respective set based on whether the parity value is even or odd.

In another aspect, the present application describes a method of encoding a bitstream of video by encoding sign bits for coefficients for a transform unit. The method includes, for each of two or more non-overlapping sets of coefficients for the transform unit, summing an absolute value of the coefficients for that set to obtain a parity value; determining that a sign of one of the coefficients in that set does not correspond to the parity value; and adjusting a level of a coefficient in that set by one in order to change the parity value to correspond to the sign of one of the coefficients.

In yet another aspect, the present application provides a method of decoding a bitstream of encoded video by reconstructing coefficients for a transform unit, wherein the transform unit is partitioned into coefficient groups each containing a respective set of coefficients, and each of the non-zero coefficients having a sign bit indicating whether the coefficient is positive or negative. The method includes determining, for a coefficient group in the transform unit, whether that coefficient group is to use sign bit hiding to encode a sign bit for a syntax element using the sum of absolute values of the coefficients in that coefficient group; for each coefficient group in the transform unit that is to use sign bit hiding, summing an absolute value of the coefficients in that coefficient group; and based on whether the absolute value is even or odd, assigning a sign to said sign bit for said syntax element.

In a further aspect, the present application describes encoders and decoders configured to implement such methods of encoding and decoding.

In yet a further aspect, the present application describes non-transitory computer-readable media storing computer-executable program instructions which, when executed, configured a processor to perform the described methods of encoding and/or decoding.

Other aspects and features of the present application will be understood by those of ordinary skill in the art from a review of the following description of examples in conjunction with the accompanying figures.

In the description that follows, some example embodiments are described with reference to the H.264 standard for video coding and/or the developing MPEG-H standard. Those ordinarily skilled in the art will understand that the present application is not limited to H.264/AVC or MPEG-H but may be applicable to other video coding/decoding standards, including possible future standards, multi-view coding standards, scalable video coding standards, and reconfigurable video coding standards.

In the description that follows, when referring to video or images the terms frame, picture, slice, tile and rectangular slice group may be used somewhat interchangeably. Those of skill in the art will appreciate that, in the case of the H.264 standard, a frame may contain one or more slices. It will also be appreciated that certain encoding/decoding operations are performed on a frame-by-frame basis, some are performed on a slice-by-slice basis, some picture-by-picture, some tile-by-tile, and some by rectangular slice group, depending on the particular requirements or terminology of the applicable image or video coding standard. In any particular embodiment, the applicable image or video coding standard may determine whether the operations described below are performed in connection with frames and/or slices and/or pictures and/or tiles and/or rectangular slice groups, as the case may be. Accordingly, those ordinarily skilled in the art will understand, in light of the present disclosure, whether particular operations or processes described herein and particular references to frames, slices, pictures, tiles, rectangular slice groups are applicable to frames, slices, pictures, tiles, rectangular slice groups, or some or all of those for a given embodiment. This also applies to transform units, coding units, groups of coding units, etc., as will become apparent in light of the description below.

The present application describes example processes and devices for encoding and decoding sign bits for the non-zero coefficients of a transform unit. The non-zero coefficients are identified by a significance map. A significance map is a block, matrix, group, or set of flags that maps to, or corresponds to, a transform unit or a defined unit of coefficients (e.g. several transform units, a portion of a transform unit, or a coding unit). Each flag indicates whether the corresponding position in the transform unit or the specified unit contains a non-zero coefficient or not. In existing standards, these flags may be referred to as significant-coefficient flags. In existing standards, there is one flag per coefficient from the DC coefficient to the last significant coefficient in a scan order, and the flag is a bit that is zero if the corresponding coefficient is zero and is set to one if the corresponding coefficient is non-zero. The term "significance map" as used herein is intended to refer to a matrix or ordered set of significant-coefficient flags for a transform unit, as will be understood from the description below, or a defined unit of coefficients, which will be clear from the context of the applications.

It will be understood, in light of the following description, that the multi-level encoding and decoding structure might be applied in certain situations, and those situations may be determined from side information like video content type (natural video or graphics as identified in sequence, picture, or slice headers). For example, two levels may be used for natural video, and three levels may be used for graphics (which is typically much more sparse). Yet another possibility is to provide a flag in one of the sequence, picture, or slice headers to indicate whether the structure has one, two, or three levels, thereby allowing the encoder the flexibility of choosing the most appropriate structure for the present content. In another embodiment, the flag may represent a content type, which would be associated with the number of levels. For example, a content of type "graphic" may feature three levels.

Figure 2:
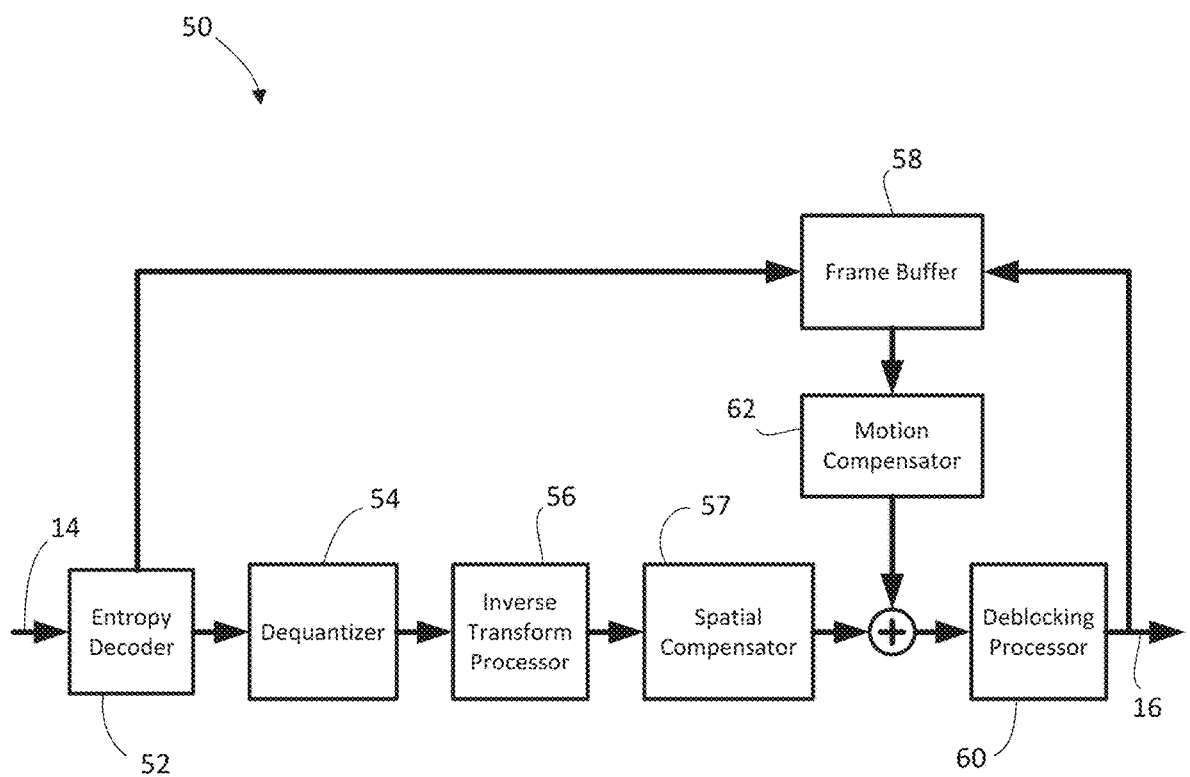
FIG. 2 shows, in block diagram form, a decoder for decoding video.

Reference is now made to FIG. 1, which shows, in block diagram form, an encoder 10 for encoding video. Reference is also made to FIG. 2, which shows a block diagram of a decoder 50 for decoding video. It will be appreciated that the encoder 10 and decoder 50 described herein may each be implemented on an application-specific or general purpose computing device, containing one or more processing elements and memory. The operations performed by the encoder 10 or decoder 50, as the case may be, may be implemented by way of application-specific integrated circuit, for example, or by way of stored program instructions executable by a general purpose processor. The device may include additional software, including, for example, an operating system for controlling basic device functions. The range of devices and platforms within which the encoder 10 or decoder 50 may be implemented will be appreciated by those ordinarily skilled in the art having regard to the following description.

The encoder 10 receives a video source 12 and produces an encoded bitstream 14. The decoder 50 receives the encoded bitstream 14 and outputs a decoded video frame 16. The encoder 10 and decoder 50 may be configured to operate in conformance with a number of video compression standards. For example, the encoder 10 and decoder 50 may be H.264/AVC compliant. In other embodiments, the encoder 10 and decoder 50 may conform to other video compression standards, including evolutions of the H.264/AVC standard, like MPEG-H.

The encoder 10 includes a spatial predictor 21, a coding mode selector 20, transform processor 22, quantizer 24, and entropy encoder 26. As will be appreciated by those ordinarily skilled in the art, the coding mode selector 20 determines the appropriate coding mode for the video source, for example whether the subject frame/slice is of I, P, or B type, and whether particular coding units (e.g. macroblocks, coding units, etc.) within the frame/slice are inter or intra coded. The transform processor 22 performs a transform upon the spatial domain data. In particular, the transform processor 22 applies a block-based transform to convert spatial domain data to spectral components. For example, in many embodiments a discrete cosine transform (DCT) is used. Other transforms, such as a discrete sine transform or others may be used in some instances. The block-based transform is performed on a coding unit, macroblock or sub-block basis, depending on the size of the macroblocks or coding units. In the H.264 standard, for example, a typical 16×16 macroblock contains sixteen 4×4 transform blocks and the DCT process is performed on the 4×4 blocks. In some cases, the transform blocks may be 8×8, meaning there are four transform blocks per macroblock. In yet other cases, the transform blocks may be other sizes. In some cases, a 16×16 macroblock may include a non-overlapping combination of 4×4 and 8×8 transform blocks.

Applying the block-based transform to a block of pixel data results in a set of transform domain coefficients. A "set" in this context is an ordered set in which the coefficients have coefficient positions. In some instances the set of transform domain coefficients may be considered as a "block" or matrix of coefficients. In the description herein the phrases "set of transform domain coefficients" or a "block of transform domain coefficients" are used interchangeably and are meant to indicate an ordered set of transform domain coefficients.

The set of transform domain coefficients is quantized by the quantizer 24. The quantized coefficients and associated information are then encoded by the entropy encoder 26.

The block or matrix of quantized transform domain coefficients may be referred to herein as a "transform unit" (TU). In some cases, the TU may be non-square, e.g. a non-square quadrature transform (NSQT).

Intra-coded frames/slices (i.e. type I) are encoded without reference to other frames/slices. In other words, they do not employ temporal prediction. However intra-coded frames do rely upon spatial prediction within the frame/slice, as illustrated in FIG. 1 by the spatial predictor 21. That is, when encoding a particular block the data in the block may be compared to the data of nearby pixels within blocks already encoded for that frame/slice. Using a prediction algorithm, the source data of the block may be converted to residual data. The transform processor 22 then encodes the residual data. H.264, for example, prescribes nine spatial prediction modes for 4×4 transform blocks. In some embodiments, each of the nine modes may be used to independently process a block, and then rate-distortion optimization is used to select the best mode.

The H.264 standard also prescribes the use of motion prediction/compensation to take advantage of temporal prediction. Accordingly, the encoder 10 has a feedback loop that includes a de-quantizer 28, inverse transform processor 30, and deblocking processor 32. The deblocking processor 32 may include a deblocking processor and a filtering processor. These elements mirror the decoding process implemented by the decoder 50 to reproduce the frame/slice. A frame store 34 is used to store the reproduced frames. In this manner, the motion prediction is based on what will be the reconstructed frames at the decoder 50 and not on the original frames, which may differ from the reconstructed frames due to the lossy compression involved in encoding/decoding. A motion predictor 36 uses the frames/slices stored in the frame store 34 as source frames/slices for comparison to a current frame for the purpose of identifying similar blocks. Accordingly, for macroblocks or coding units to which motion prediction is applied, the "source data" which the transform processor 22 encodes is the residual data that comes out of the motion prediction process. For example, it may include information regarding the reference frame, a spatial displacement or "motion vector", and residual pixel data that represents the differences (if any) between the reference block and the current block. Information regarding the reference frame and/or motion vector may not be processed by the transform processor 22 and/or quantizer 24, but instead may be supplied to the entropy encoder 26 for encoding as part of the bitstream along with the quantized coefficients.

Those ordinarily skilled in the art will appreciate the details and possible variations for implementing video encoders.

The decoder 50 includes an entropy decoder 52, dequantizer 54, inverse transform processor 56, spatial compensator 57, and deblocking processor 60. The deblocking processor 60 may include deblocking and filtering processors. A frame buffer 58 supplies reconstructed frames for use by a motion compensator 62 in applying motion compensation. The spatial compensator 57 represents the operation of recovering the video data for a particular intra-coded block from a previously decoded block.

The bitstream 14 is received and decoded by the entropy decoder 52 to recover the quantized coefficients. Side information may also be recovered during the entropy decoding process, some of which may be supplied to the motion compensation loop for use in motion compensation, if applicable. For example, the entropy decoder 52 may recover motion vectors and/or reference frame information for inter-coded macroblocks.

The quantized coefficients are then dequantized by the dequantizer 54 to produce the transform domain coefficients, which are then subjected to an inverse transform by the inverse transform processor 56 to recreate the "video data". It will be appreciated that, in some cases, such as with an intra-coded macroblock or coding unit, the recreated "video data" is the residual data for use in spatial compensation relative to a previously decoded block within the frame. The spatial compensator 57 generates the video data from the residual data and pixel data from a previously decoded block. In other cases, such as inter-coded macroblocks or coding units, the recreated "video data" from the inverse transform processor 56 is the residual data for use in motion compensation relative to a reference block from a different frame. Both spatial and motion compensation may be referred to herein as "prediction operations".

The motion compensator 62 locates a reference block within the frame buffer 58 specified for a particular inter-coded macroblock or coding unit. It does so based on the reference frame information and motion vector specified for the inter-coded macroblock or coding unit. It then supplies the reference block pixel data for combination with the residual data to arrive at the reconstructed video data for that coding unit/macroblock.

A deblocking/filtering process may then be applied to a reconstructed frame/slice, as indicated by the deblocking processor 60. After deblocking/filtering, the frame/slice is output as the decoded video frame 16, for example for display on a display device. It will be understood that the video playback machine, such as a computer, set-top box, DVD or Blu-Ray player, and/or mobile handheld device, may buffer decoded frames in a memory prior to display on an output device.

It is expected that MPEG-H-compliant encoders and decoders will have many of these same or similar features.

Quantized Transform Domain Coefficient Encoding and Decoding

As noted above, the entropy coding of a block or set of quantized transform domain coefficients includes encoding the significance map (e.g. a set of significant-coefficient flags) for that block or set of quantized transform domain coefficients. The significance map is a binary mapping of the block indicating in which positions (from the DC position to the last significant-coefficient position) non-zero coefficients appear. The significance map may be converted to a vector in accordance with the scan order (which may be vertical, horizontal, diagonal, zig zag, or any other scan order prescribed by the applicable coding standard). The scan is typically done in "reverse" order, i.e. starting with the last significant coefficient and working back through the significant map in reverse direction until the significant-coefficient flag in the upper-left corner at [0,0] is reached. In the present description, the term "scan order" is intended to mean the order in which flags, coefficients, or groups, as the case may be, are processed and may include orders that are referred to colloquially as "reverse scan order".

Each significant-coefficient flag is then entropy encoded using the applicable context-adaptive coding scheme. For example, in many applications a context-adaptive binary arithmetic coding (CABAC) scheme may be used.

With 16×16 and 32×32 significance maps, the context for a significant-coefficient flag is (in most cases) based upon neighboring significant-coefficient flag values. Among the contexts used for 16×16 and 32×32 significance maps, there are certain contexts dedicated to the bit position at [0,0] and (in some example implementations) to neighboring bit positions, but most of the significant-coefficient flags take one of four or five contexts that depend on the cumulative values of neighboring significant-coefficient flags. In these instances, the determination of the correct context for a significant-coefficient flag depends on determining and summing the values of the significant-coefficient flags at neighboring locations (typically five locations, but it could be more or fewer in some instances).

The significant-coefficient levels for those non-zero coefficients may then be encoded. In one example implementation, the levels may be encoded by first encoding a map of those non-zero coefficients having an absolute value level greater than one. Another map may then be encoded of those non-zero coefficients having a level greater than two. The value or level of any of the coefficients having an absolute value greater than two is then encoded. In some cases, the value encoded may be the actual value minus three.

The sign of the non-zero coefficients is also encoded. Each non-zero coefficient has a sign bit indicating whether the level of that non-zero coefficient is negative or positive. A proposal has been made to hide the sign bit for the first coefficient in the transform unit: Clare, Gordon, et al., "Sign Data Hiding", JCTVC-G271, 7$^{th}$ Meeting, Geneva, 21-30 Nov. 2011. Under this proposal the sign of the first coefficient in the transform unit is encoded by way of the parity of the sum of quantized coefficients in the transform unit. In the event that the parity does not correspond to the actual sign of the first coefficient, then the encoder must adjust the level of one of the coefficients up or down by 1 in order to adjust the parity. RDOQ is to be used to determine which coefficient to adjust and in what direction.

Figure 3:
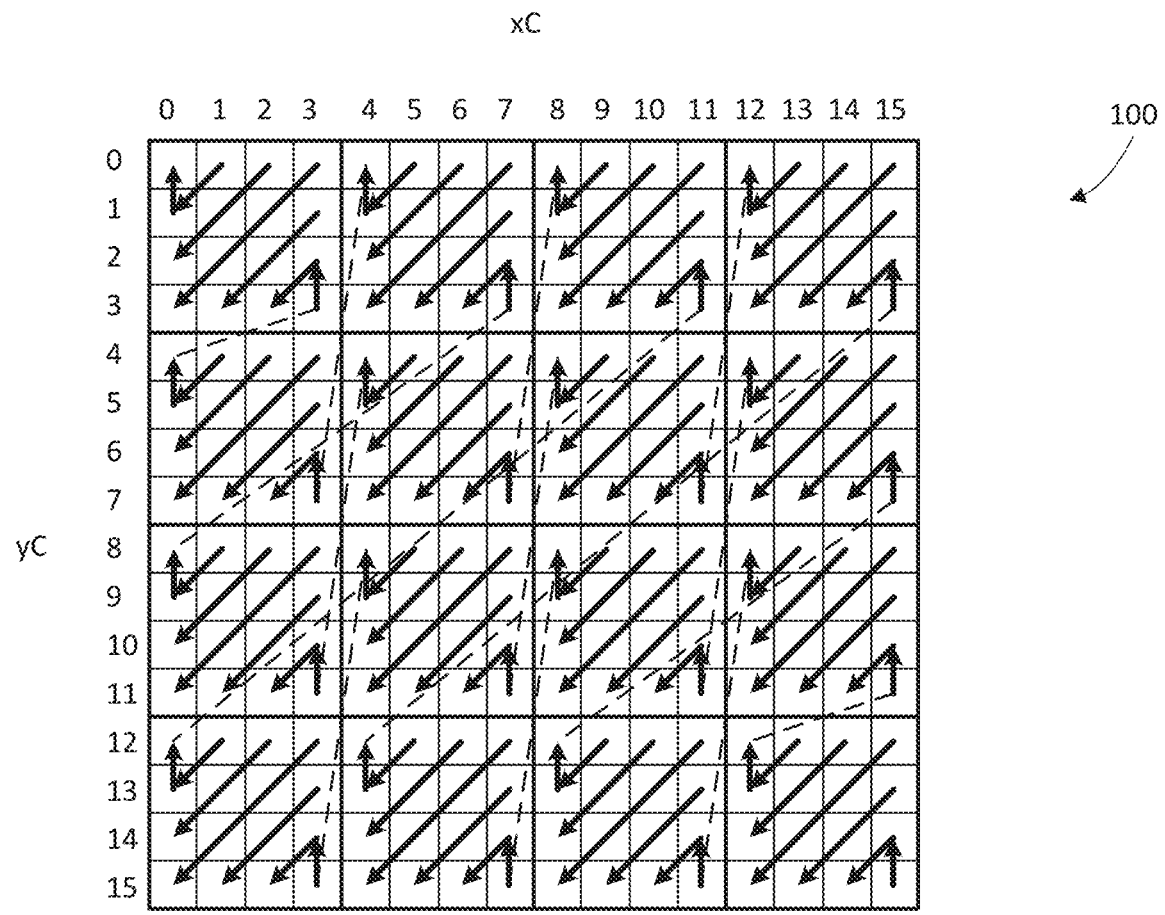
FIG. 3 shows, an example of a multi-level scan order for a 16×16 transform unit.

Some prior work has focused on using multi-level significance maps. Reference is now made to FIG. 3, which shows a 16×16 transform unit 100 with a multi-level diagonal scan order illustrated. The transform unit 100 is partitioned into sixteen contiguous 4×4 coefficient groups or "sets of significant-coefficient flags". Within each coefficient group, a diagonal scan order is applied within the group, rather than across the whole transform unit 100. The sets or coefficient groups themselves are processed in a scan order, which in this example implementation is also a diagonal scan order. It will be noted that the scan order in this example is illustrated in "reverse" scan order; that is, the scan order is shown progressing from the bottom-right coefficient group in a downward-left diagonal direction towards the upper-left coefficient group. In some implementations the same scan order may be defined in the other direction; that is, progressing in am upwards-right diagonal direction and when applied during encoding or decoding may be applied in a "reverse" scan order.

The use of multi-level significance maps involves the encoding of an L1 or higher-level significance map that indicates which coefficient groups may be expected to contain non-zero significant-coefficient flags, and which coefficient groups contain all zero significant-coefficient flags. The coefficient groups that may be expected to contain non-zero significant-coefficient flags have their significant-coefficient flags encoded, whereas the coefficient groups that contain all zero significant-coefficient flags are not encoded (unless they are groups that are encoded because of a special case exception because they are presumed to contain at least one non-zero significant-coefficient flag). Each coefficient group has a significant-coefficient-group flag (unless a special case applies in which that coefficient group has a flag of a presumed value, such as the group containing the last significant coefficient, the upper left group, etc.).

The use of multi-level significance maps facilitates the modular processing of residual data for encoding and decoding.

Larger TUs present an opportunity to hide multiple sign bits. The TU may be divided or partitioned into sets of non-zero coefficients and a sign bit may be hidden for each set of non-zero coefficients using the parity of the sum of non-zero coefficients in that set. In one embodiment, the set of non-zero coefficients may be made to correspond to the coefficient groups defined for multi-level significance maps.

A single threshold may be used to determine whether to hide a sign bit for a certain set of non-zero coefficients, irrespective of data type. In one example, the threshold test is based on the number of coefficients between the first non-zero coefficient and last non-zero coefficient in the set. That is, whether there are at least a threshold number of coefficients between the first and last non-zero coefficients in the set. In another example, the test may be based on there being at least a threshold number of non-zero coefficients in the set. In yet another embodiment, the test may be based on the sum of the absolute value of the non-zero coefficients in the set exceeding a threshold. In a yet further embodiment, a combination of these tests may be applied; that is, there must be at least a minimum number of coefficients in the set and the cumulative absolute value of the coefficients must exceed a threshold value. Variations on these threshold tests may also be employed.

Figure 4:
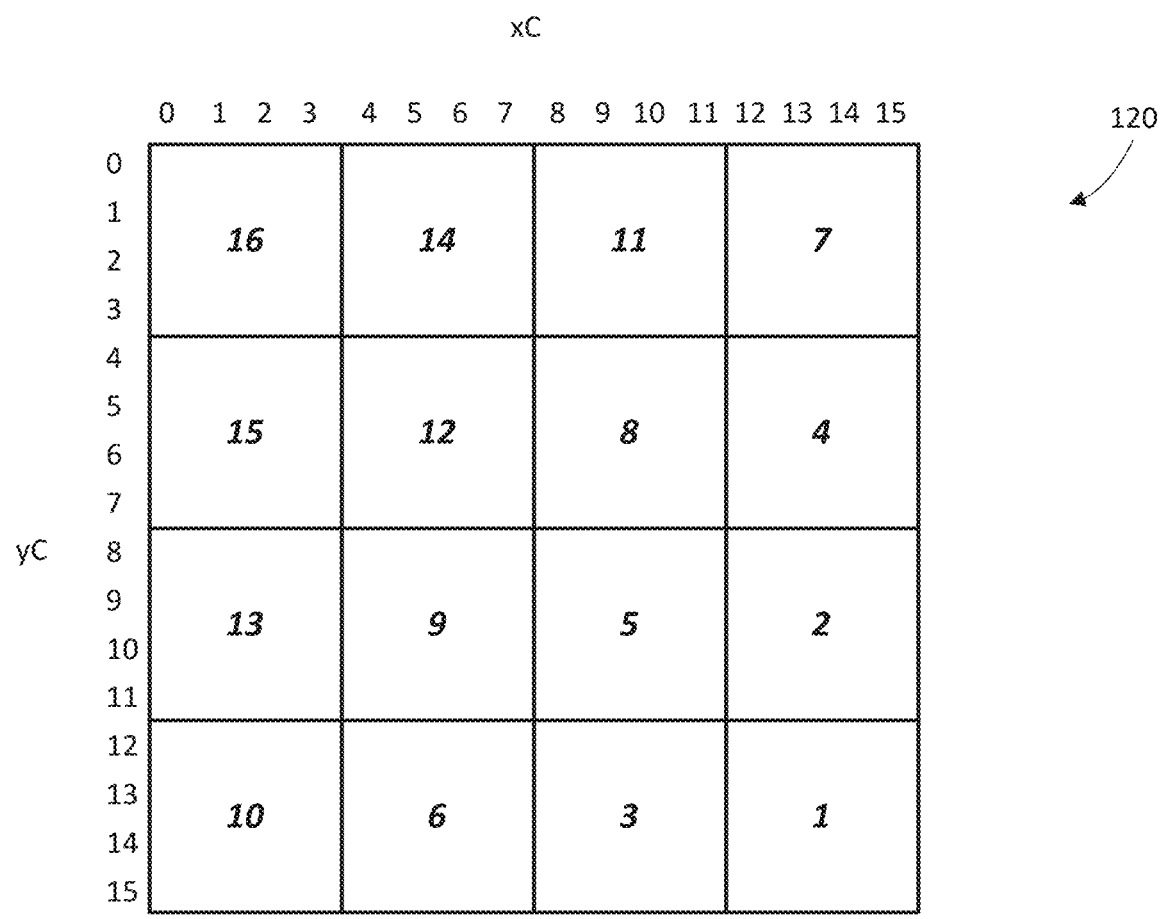
FIG. 4 shows an example 16×16 transform unit partitioned into coefficient groups numbered in reverse group-level scan order.

Reference is now made to FIG. 4, which shows an example 16×16 transform unit 120. The transform unit 120 is divided into 4×4 coefficient groups, i.e. sixteen sets of coefficients. The coefficient groups are numbered 1, 2, 3, . . . 16 in the order in which they are processed, e.g. reverse diagonal scan order.

In a first embodiment, each coefficient group is a set of coefficients for the purpose of sign bit hiding. That is, each coefficient group is tested against a threshold to determine if the coefficient group is suitable for sign bit hiding. As noted above, the test may be that the coefficient group contains at least a minimum number of coefficients between the first non-zero coefficient and last non-zero coefficient within that coefficient group.

Figure 5:
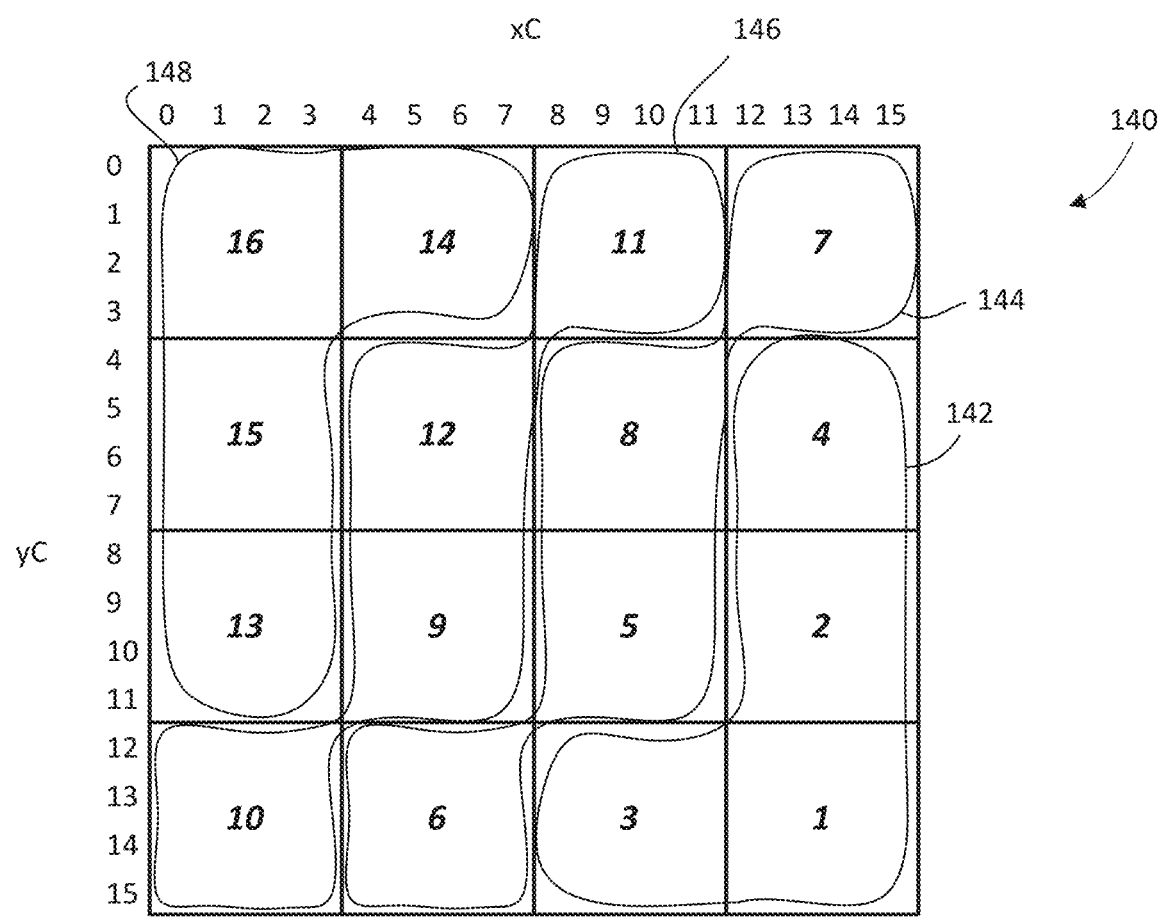
FIG. 5 shows one example of a transform unit in which four groups of coefficient groups are formed for sign bit hiding.

In a second embodiment, the sets of coefficients for sign bit hiding are formed by grouping coefficient groups. FIG. 5 shows a 16×16 TU 140 on which is illustrated an example grouping of coefficient groups into four sets of coefficients. In this example, each set of coefficients for the purpose of sign bit hiding contains four coefficient groups. The four coefficient groups in each set are consecutive groups in the scan order. For instance, the first set of coefficients 142 contains coefficient groups 16, 15, 14, and 13. The second set of coefficients 144 contains coefficient groups 12, 11, 10, and 9. The third set of coefficients 146 contains coefficient groups 8, 7, 6, and 5. Finally, the fourth set of coefficients 148 contains coefficient groups 4, 3, 2, and 1. In this embodiment, a sign bit may be hidden for each set of coefficients. That is, up to four sign bits may be hidden per TU 140.

For each set of coefficients 142, 144, 146, 148, the number of coefficients between the first and last non-zero coefficient (or the number of non-zero coefficients, or the cumulative total value of those coefficients) is tested against the threshold to determine whether to hide a sign bit for that set. The parity of the sum of absolute values of those coefficients in the set is the mechanism through which sign bit is hidden. If the parity does not correspond to the sign to be hidden, then the parity is adjusted by adjusting the level of one of the coefficients in the set.

Figure 6:
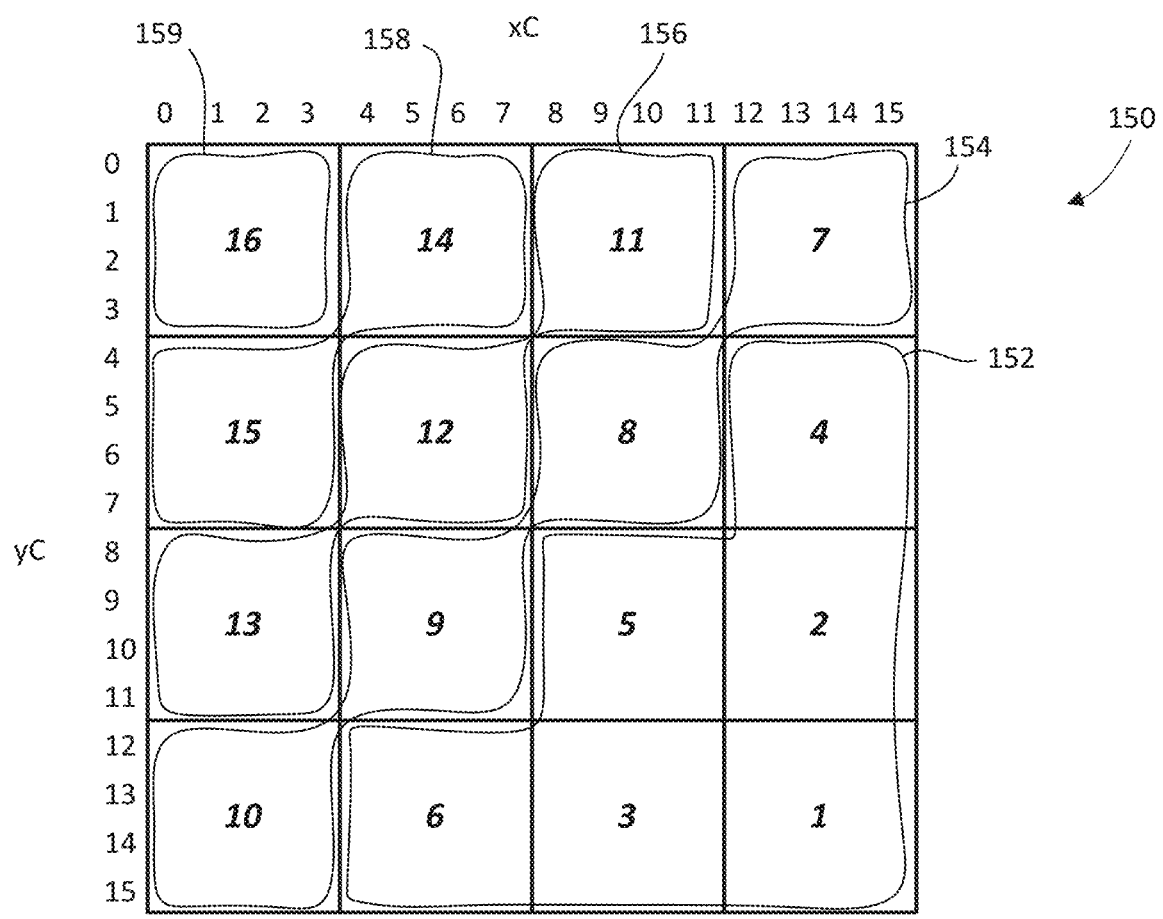
FIG. 6 illustrates another example of a grouping of coefficient groups for sign bit hiding.

FIG. 6 illustrates a third embodiment of sets of coefficients for sign bit hiding with a 16×16 TU 150. In this embodiment, the sets are again formed on the basis of coefficient groups, but the sets do not necessarily contain the same number of coefficients or coefficient groups. For example, in this illustration five sets of coefficients are defined. The first set 152 contains coefficient groups 1 to 6. The second set 154 contains four coefficient groups: 7, 8, 9, and 10. The third set 156 contains coefficient groups 11, 12, and 13. The fourth set 158 contains coefficient groups 14 and 15. The fifth set 159 contains just the upper left coefficient group 16. It will be appreciated that this embodiment provides for larger sets of coefficients in areas of the transform unit 150 for which there are likely to be fewer non-zero coefficients, and smaller sets of coefficients in the areas of the transform unit 150 in which non-zero coefficients are more common. Note that the above embodiments could apply to 32×32 or larger TU sizes as well as an 8×8 TU size as long as a coefficient group structure is applied to those TUs.

Figure 7:
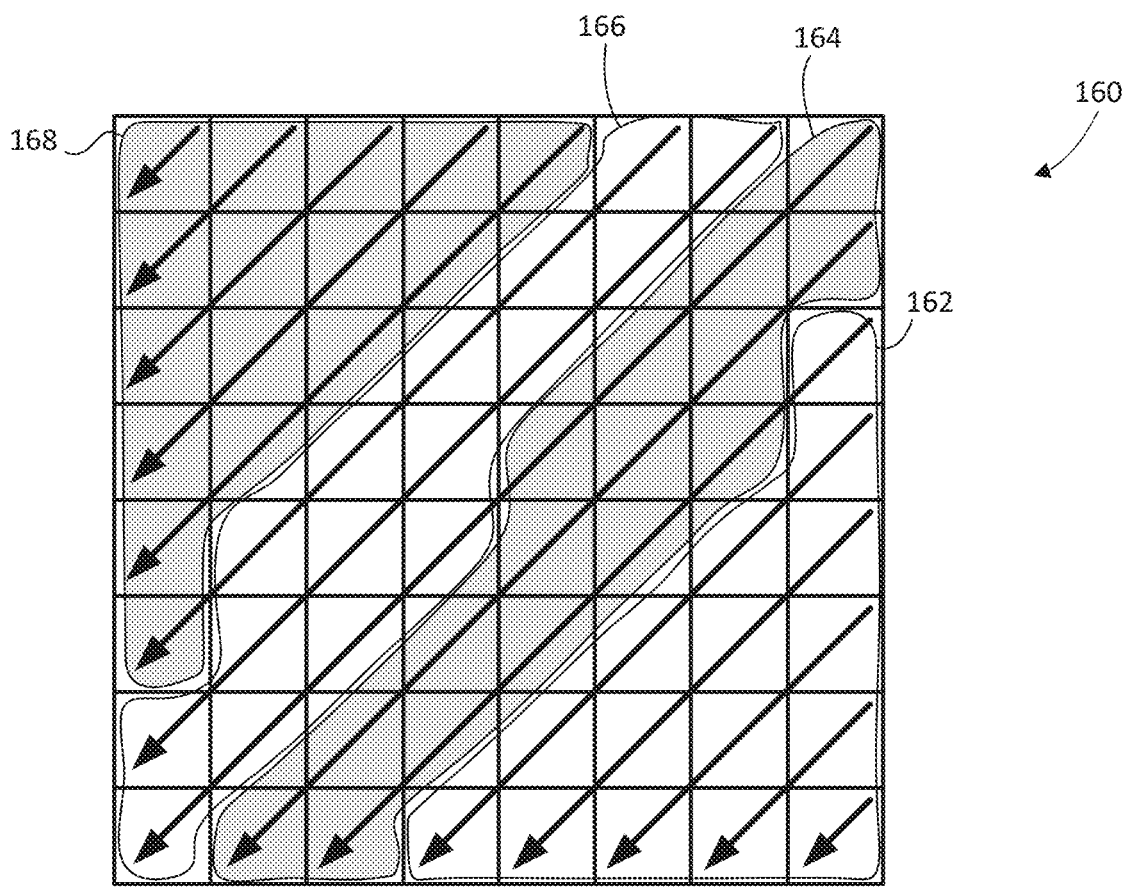
FIG. 7 shows yet another example of a grouping of coefficient groups for sign bit hiding.

FIG. 7 illustrates a fourth embodiment, in which sets of coefficients for sign bit hiding within an 8×8 transform unit 160 are formed without adhering to the coefficient group structure. The 8×8 transform unit may, or may not, have coefficient group partitioning for the purpose of significance map encoding. In any event, in this embodiment a transform-unit-based diagonal scan is used for processing the coefficients for sign bit encoding and hiding. In this case, the sets of coefficients are formed so as to group consecutive coefficients in the scan order. For example, in this illustration the transform unit 160 is grouped into four sets of coefficients, each containing 16 consecutive coefficients in the scanning order. The groups are labeled 162, 164, 166, and 168 in FIG. 7.

In yet another embodiment, the sets of coefficients may not adhere to the scan order. That is, each set may include some coefficients from higher frequency positions in the transform unit and some coefficients from lower frequency positions in the transform unit. All coefficients in these sets may not necessarily be adjacent in the scan order.

Figure 8:
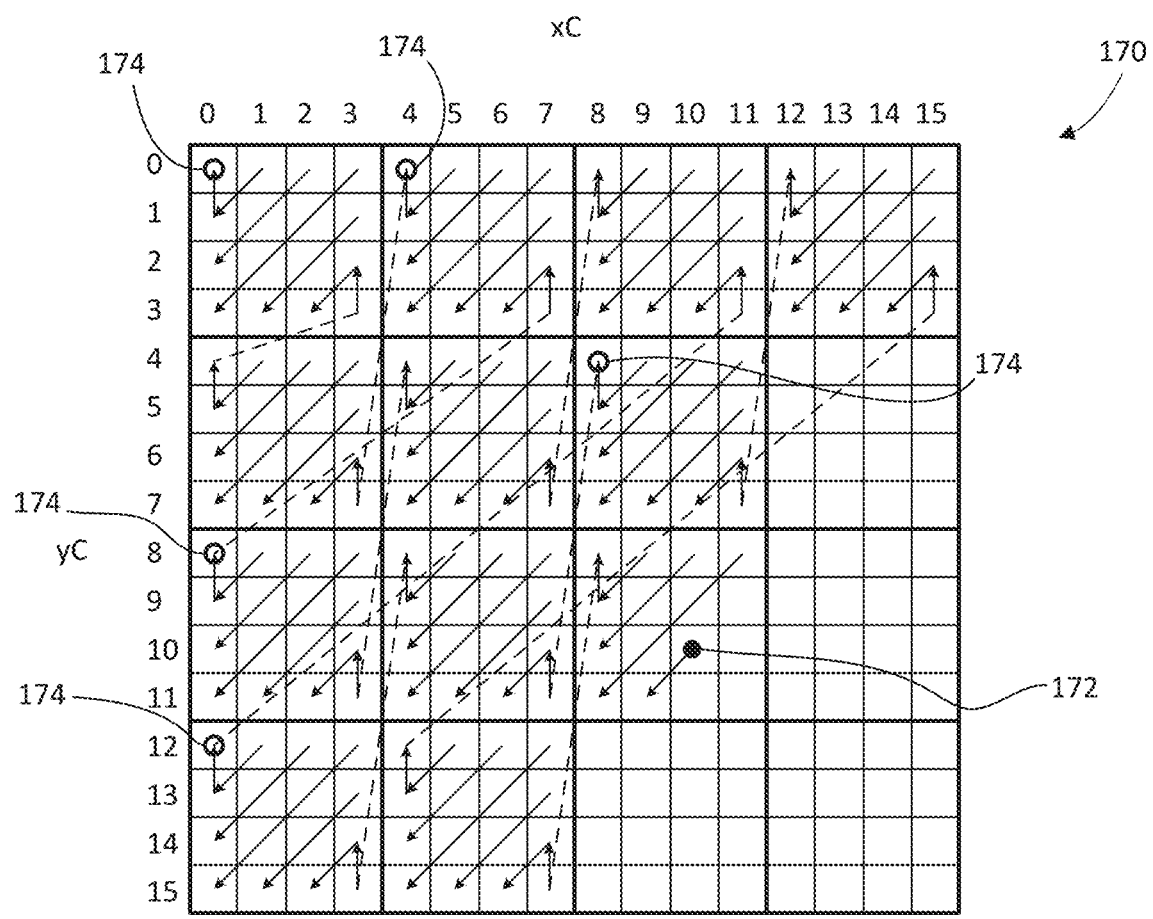
FIG. 8 illustrates an example of dynamically forming sets of coefficients for sign bit hiding.

FIG. 8 shows a fifth embodiment, in which sets of coefficients for sign bit hiding within a 16×16 transform unit 170 are dynamically formed, using the coefficient group structure and scan order. In this embodiment, rather than a fixed set of coefficients predefined based on the transform unit size and scan order, the encoder and decoder form the sets by following the scan order and tracking whatever quantity is measured against a threshold value until the threshold value is met. Once the threshold is met, then a sign bit is hidden for the coefficient group which the encoder or decoder is then processing.

As an example, FIG. 8 illustrates a last-significant coefficient within the coefficient group [2, 2]. In scan order, the encoder and decoder then move to coefficient groups [1, 3], [3, 0], and [2, 1], in turn. Whilst processing coefficients in coefficient group [2, 1], the threshold is met. Accordingly, the sign bit for the last non-zero coefficient to be processed in reverse scan order in the coefficient group [2, 1] (the most upper-left non-zero coefficient in the group) is hidden in the parity of the cumulative absolute value of coefficients from the last-significant coefficient through to and including all coefficients in the current coefficient group [2, 1]. The threshold test in this example may be based on there being a minimum number of non-zero coefficients, or the absolute value of the coefficients exceeding some threshold value. The reference number 174 indicates a sign bit hiding operation with respect to the 'last' or upper-leftmost coefficient in a particular coefficient group.

In a sixth embodiment, sign bit hiding is done on the basis of coefficient groups, and the criteria used to determine if a coefficient group is suitable for sign bit hiding are dynamically adjusted according to the previously decoded coefficient groups. As an example, if either the coefficient group immediately to its right or the coefficient group immediately to its bottom has a non-zero coefficient, the current coefficient group is determined to be suitable for sign bit hiding as long as it contains a minimum of two non-zero coefficients The coefficient group may also be determined to be suitable if it contains at least a minimum number of coefficients between the first non-zero coefficient and last non-zero coefficient within that coefficient group, as described in some of the embodiments above.

It will be appreciated that in some of the foregoing embodiments, a sign bit may be hidden in one coefficient group based on a parity value that relies on coefficients in another coefficient group. In other words, the sign value of a coefficient in one coefficient group may be hidden in the parity by way of a level change to a coefficient in another coefficient group.

Furthermore, it will be appreciated in that in some of the foregoing embodiments, a sign bit hidden in a set of coefficients may be from a different syntax element like a motion vector difference flag (e.g. mvd_sign_flag).

At the encoder side, the decision is made regarding which coefficient to adjust in order to hide a sign bit in a case where the parity value does not correspond to the sign. Where the parity value needs to be adjusted, a coefficient level must be increased or decreased by 1 in order to change the parity.

In one embodiment, the first step in the process of adjusting a coefficient level is to determine a search range, i.e., a starting position and an end position in the scanning order. The coefficients within this range are then evaluated and one is selected to be changed. In one exemplary embodiment, the search range may be from the first non-zero coefficient to the last coefficient in the scanning order.

With the use of multi-level significance maps, the ending position for a search range for a subset may be changed to utilize the block-level information. Specifically, if one subset contains the very last non-zero coefficient in the whole TU, (the so-called global last, or Last Significant Coefficient), the search range may be established as the first non-zero coefficient to the last non-zero coefficient. For other subsets, the search range may be extended to a range from the first non-zero coefficient to the end of the current sub-block.

In one embodiment, the starting position may be extended to conditionally include un-quantized coefficients ahead of the first non-zero quantized coefficient. Specifically, consider all coefficients before the quantization. Un-quantized coefficients that have the same sign as the sign to be hidden will be included in the search. For un-quantized coefficients from position zero to the position of the first nonzero quantized coefficient, the cost of changing a quantized coefficient from zero to one will be evaluated and tested in the search.

Another issue in the process for adjusting a coefficient level is to define the cost calculation used to assess the impact of an adjustment. When computational complexity is a concern, the cost may based on the distortion and rate may not be taken into account, in which case the search is to minimize the distortion. On the other hand, when computational complexity is not an over-riding concern, the cost may include both the rate and distortion so as to minimize the rate distortion cost.

If RDOQ is enabled, then RDOQ may be used to adjust the level. However, in many cases, the computational complexity of RDOQ may be undesirable and RDOQ may not be enabled. Accordingly, in some embodiments a simplified rate-distortion analysis may be applied at the encoder to implement the sign bit hiding.

Each coefficient between the first non-zero coefficient in the set and the last non-zero coefficient in the set may be tested by roughly calculating distortion from increasing the coefficient by 1 and from decreasing the coefficient by 1. In general terms, the a coefficient value of u has a real value of u+δ. The distortion is given by $(δq)^2$. If that coefficient u is adjusted up by 1 to u+1, then the resulting distortion may be estimated as:

$$q^2(1-2δ)$$

If the coefficient u is adjusted down by 1 to u−1, then the resulting distortion may be estimated as:

$$q^2(1+2δ)$$

It will be recognized that for the inter-coded case, the quantization distortion δ is in the range [−⅙ to +⅚] when RDOQ is off. In the case of intra-coded blocks, the quantization distortion δ is in the range [−⅓ to +⅔] when RDOQ is off. When RDOQ is on, the range of δ will vary. However, the above calculation of distortion increase is still valid, regardless of the range of δ.

The encoder may also make rough estimates regarding rate cost for the various coefficients using a set of logic rules, i.e. a predefined rate cost metric. For example, the predefined rate cost metric, in one embodiment, may include:

$u+1 (u≠0$ and $u≠−1) → 0.5$ bits $u−1 (u≠0$ and $u≠+1) → −0.5$ bits $u=1$ or $−1$ and changed to $0 → −1−0.5−0.5$ bits $u=0$ and changed to $1$ or $−1 → 1+0.5+0.5$ bits where the cost of a sign flag is estimated to be 1 bit, the cost of a significant coefficient flag is estimated to be 0.5 bits, and the cost increase from u to u+1 is estimated to be 0.5 bits.

Other rules or estimates may be used in other embodiments.

Figure 9:
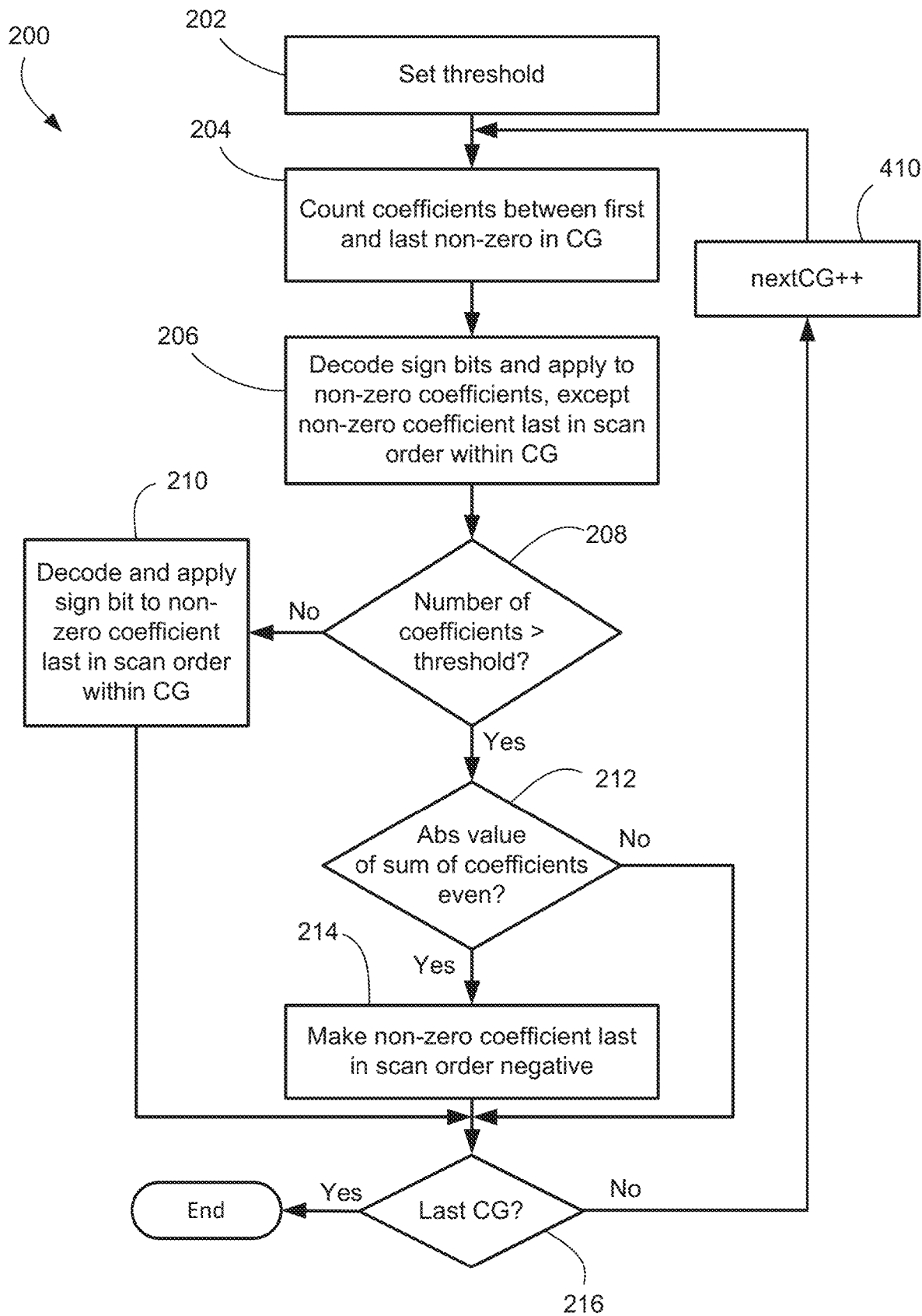
FIG. 9 shows, in flowchart form, an example process for sign bit hiding.

Reference is now made to FIG. 9, which shows an example process 200 for decoding video data with coefficient-group-based sign bit hiding. The process 200 is based on the second embodiment described above. After reviewing the description, alterations and modifications to the process 200 to implement other embodiments described will be appreciated by those ordinarily skilled in the art.

A threshold value is set in operation 202. In some embodiments, this threshold value may be predetermined or pre-configured within the decoder. In other embodiments, this value may extracted from the bitstream of encoded video data. For example, the threshold value may be in the picture header or in another location within the bitstream.

In operation 204, the decoder identifies the first non-zero position in the current coefficient group, i.e. set of coefficients, and the last non-zero position in the current coefficient group, in scan order. It then determines the number of coefficients, in scan order, between the first and last non-zero coefficients in the coefficient group.

In operation 206, the decoder decodes sign bits from the bitstream. It decodes a sign bit for every non-zero coefficient in the coefficient group except for the upper-leftmost non-zero coefficient in the coefficient group (the last non-zero coefficient in reverse scan order). The sign bits are applied to their respective non-zero coefficients. For example, if the applicable convention is that a sign bit of zero is positive and a sign bit of one is negative, then for all sign bits set to one the corresponding coefficient level is made negative.

In operation 208, the decoder evaluates whether the number of coefficients between the first non-zero coefficient and the last non-zero coefficient in scan order in the coefficient group exceeds the threshold. If not, then sign bit hiding was not used at the encoder, so in operation 210 the decoder decodes the sign bit for the upper-leftmost non-zero coefficient (last in reverse scan order) and applies it to the coefficient level. If the number of coefficients does meet the threshold, then in operation 212 the decoder assesses whether the absolute value of the sum of the coefficients in the coefficient group is even or odd, i.e. its parity. If even, then the sign of the upper-leftmost non-zero coefficient is positive and the decoder does not need to adjust it. If odd, then the sign of the upper-leftmost non-zero coefficient is negative, so in operation 214 it makes that coefficient negative.

In operation 216, the decoder determines whether it has finished processing the coefficient groups. If so, the process 200 exits. Otherwise, it moves to the next coefficient group in the group scan order in operation 218 and returns to operation 204.

In one other embodiment, the size of the set of coefficients may be reduced to a single coefficient. That is, the sign bit hiding may be single-coefficient-based sign hiding. In this embodiment, each coefficient is tested to see whether its sign information is to be hidden. One example test is to compare the magnitude of the coefficient level with a given threshold. Coefficients having a level larger than the threshold have their sign bits hidden; otherwise, convention sign bit encoding/decoding is used.

To apply the sign bit hiding in the single-coefficient case, the sign information is compared to the parity of the coefficient level. As an example even parity may correspond to positive sign and odd may correspond to negative. The encoder then adjusts the level if the level does not correspond to the sign. It will be appreciated that this technique implies that above the threshold value all negative levels are odd and all positive levels are even. In one sense this may be considered, in effect, a modification of the quantization step size for coefficients having a magnitude larger than the threshold.

An example syntax for implementing sign bit hiding is provided below. This example syntax is but one possible implementation. In this example, the sign bit hiding is applied on a coefficient-group-basis, and the threshold test is based on the number coefficients from the first non-zero coefficient in the coefficient group to the last non-zero coefficient in the coefficient group. A flag denoted sign_data_hiding is sent in the picture header to indicate whether sign bit hiding is turned on. If it is enabled, then the header also contains the parameter tsig, which is the threshold value. Example syntax is set out below:

|  | Descriptor |
|---|---|
| pic_parameter_set_rbsp( ) { |  |
|     pic_parameter_set_id | ue(v) |
|     seq_parameter_set_id | ue(v) |
|     sign_data_hiding | u(1) |
|     if ( sign_data_hiding ) { |  |
|         tsig | u(4) |
|     } |  |
|     entropy_coding_synchro | u(v) |
|     cabac_istate_reset_flag | u(1) |
|     if( entropy_coding_synchro ) |  |
|         num_substreams_minus1 | ue(v) |
| ... |  |

The following pseudo-code illustrates one example implementation of coefficient-group-based sign bit hiding:

|  | Descriptor |
|---|---|
| residual_coding_cabac( x0, y0, log2TrafoWidth, log2TrafoHeight, scanIdx, cIdx ) { |  |
|     last_significant_coeff_x_prefix | ae(v) |
|     last_significant_coeff_y_prefix | ae(v) |
|     if ( last_significant_coeff_x_prefix > 3 ) |  |
|         last_significant_coeff_x_suffix | ae(v) |
|     if ( last_significant_coeff_y_prefix > 3 ) |  |
|         last_significant_coeff_y_suffix | ae(v) |
|     numCoeff = 0 |  |
|     do { |  |
|         xC = ScanOrder[ log2TrafoWidth ][ log2TrafoHeight ][ scanIdx ][ numCoeff ][ 0 ] |  |
|         yC = ScanOrder[ log2TrafoWidth ][ log2TrafoHeight ][ scanIdx ][ numCoeff ][ 1 ] |  |
|         numCoeff++ |  |
|     } while( (xC != LastSignificantCoeffX ) || ( yC != LastSignificantCoeffY ) ) |  |
|     numLastSubset = (numCoeff − 1) >> 4 |  |
|     for( i = numLastSubset; i >= 0; i− − ) { |  |
|         offset = i << 4 |  |
|         if( max( log2TrafoWidth, log2TrafoHeight ) > 3) { |  |
|             ...... omitted |  |
|         } else { |  |
|             ...... omitted |  |
|         } |  |
|         firstNZPosInCG = 1 << 4 ; |  |
|         lastNZPosInCG = − 1 ; |  |
|         for(n = 15; n>= 0; n− − ) { |  |
|             xC = ScanOrder[ log2TrafoWidth ][ log2TrafoHeight ][ scanIdx ][ n + offset ][ 0 ] |  |
|             yC = ScanOrder[ log2TrafoWidth ][ log2TrafoHeight ] [ scanIdx ][ n + offset ][ 1 ] |  |
|             if( significant_coeff_flag[ xC ][ yC ] ) { |  |
|                 coeff_abs_level_greater1_flag[ n ] | ae(v) |
|                 if( lastNZPosInCG ==− 1) |  |
|                     lastNZPosInCG = n |  |
|                 firstNZPosInCG = n |  |
|             } |  |
|         } |  |
|         signHidden = lastNZPosInCG − firstNZPosInCG + 1 >= tsig |  |
|         for(n = 15; n >= 0; n− − ) { |  |
|             if( coeff_abs_level_greater1_flag[ n ] ) |  |
|                 coeff_abs_level_greater2_flag[ n ] | ae(v) |
|         } |  |
|         for( n = 15; n>= 0; n− −){ |  |
|             xC = ScanOrder[ log2TrafoWidth ][ log2TrafoHeight ][ scanIdx ][ n + offset ][ 0 ] |  |

-continued

```
                                                                              Descriptor
            yC = ScanOrder[ log2TrafoWidth ][ log2TrafoHeight ][ scanIdx ][ n + offset ][ 1 ]
            if( significant_coeff_flag[ xC ][ yC ] ) {
                if (!sign_data_hiding || !signHidden || n != firstNZPosInCG)
                    coeff_sign_flag[ n ]                                      ae(v)
                else
                    coeff_sign_flag[n] = 0 ;
            }
        }
        sumAbs = 0 ;
        for( n = 15; n >= firstNZPosInCG; n- - ) {
            if( coeff_abs_level_greater2_flag[ n ] )
                coeff_abs_level_minus3[ n ]                                   ae(v)
            xC = ScanOrder[ log2TrafoWidth ][ log2TrafoHeight ] [ scanIdx ][ n + offset ][ 0 ]
            yC = ScanOrder[ log2TrafoWidth ][ log2TrafoHeight ] [ scanIdx ][ n + offset ][ 1 ]
            if( significant_coeff_flag[ xC ] [ yC ] ) {
                transCoeffLevel[ x0 ][ y0 ][ cIdx ][ xC ][ yC ] =
                    ( coeff_abs_level_minus3[n] + 3) * (1 - 2 * coeff_sign_flag[ n ] )
                if (sign_data_hiding && signHidden)
                    sumAbs += coeff_abs_level_minus3[n]+3
            } else
                transCoeffLevel[ x0 ][ y0 ][ cIdx ][ xC ][ yC ] = 0
        }
        if (sign_data_hiding && signHidden && (sumAbs %2 == 1))
            transCoeffLevel[x0][y0][cIdx][xC][yC] = - transCoeffLevel[x0][y0][cIdx][xC][yC]
    }
}
```

Figure 10:
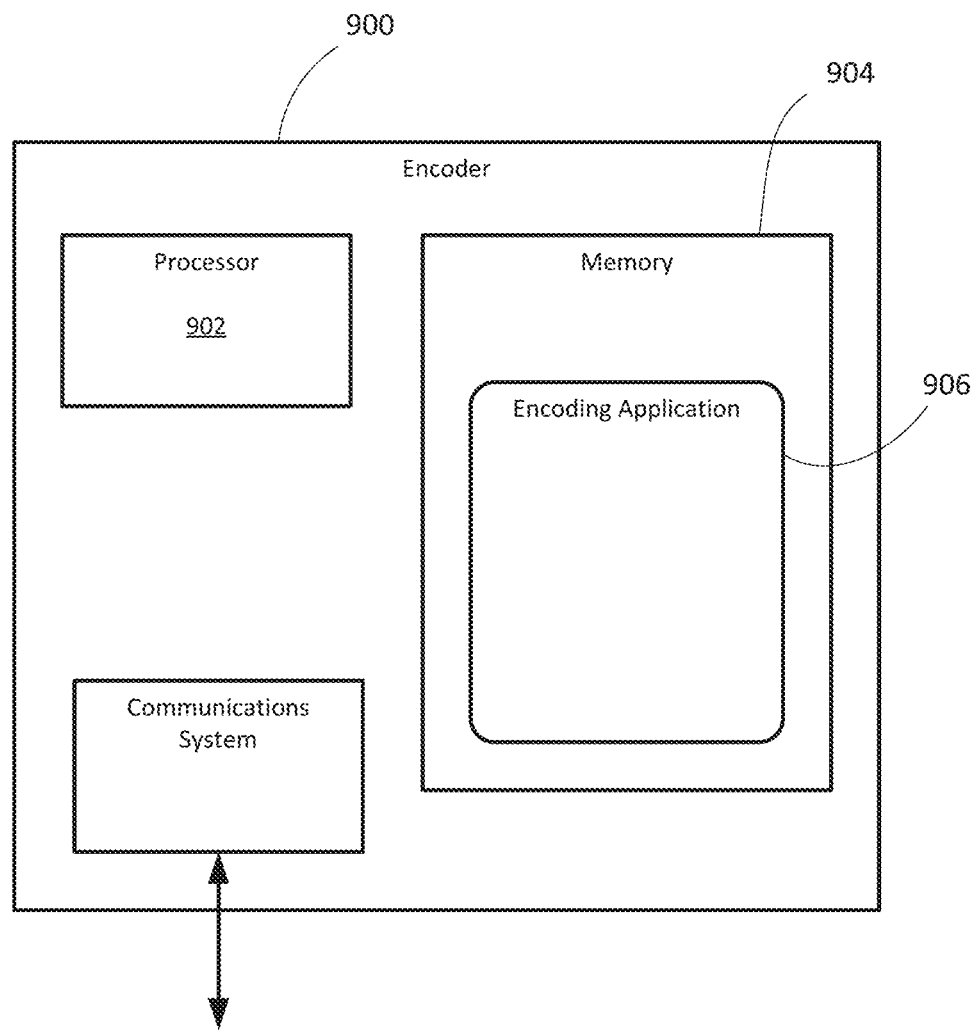
FIG. 10 shows a simplified block diagram of an example embodiment of an encoder.

Reference is now made to FIG. 10, which shows a simplified block diagram of an example embodiment of an encoder 900. The encoder 900 includes a processor 902, memory 904, and an encoding application 906. The encoding application 906 may include a computer program or application stored in memory 904 and containing instructions for configuring the processor 902 to perform operations such as those described herein. For example, the encoding application 906 may encode and output bitstreams encoded in accordance with the processes described herein. It will be understood that the encoding application 906 may be stored in on a computer readable medium, such as a compact disc, flash memory device, random access memory, hard drive, etc.

Figure 11:
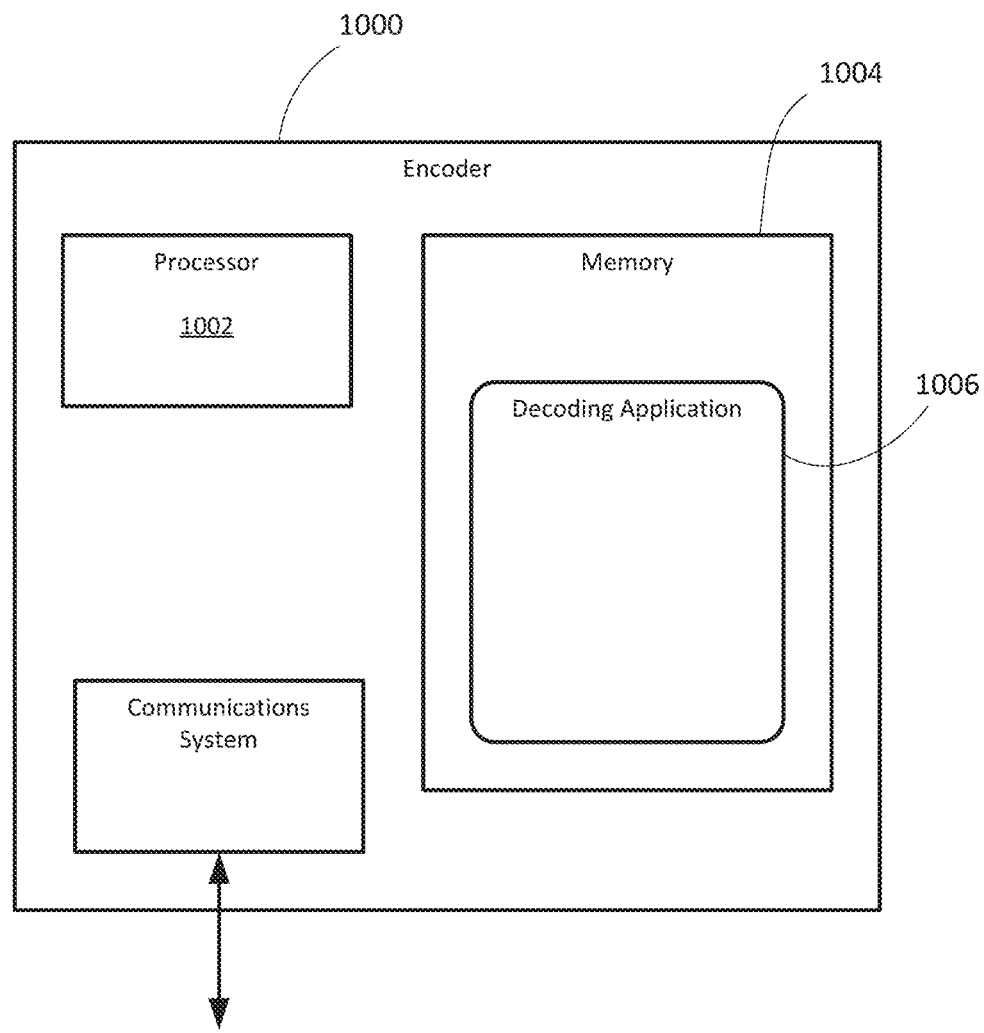
FIG. 11 shows a simplified block diagram of an example embodiment of a decoder.

Reference is now also made to FIG. 11, which shows a simplified block diagram of an example embodiment of a decoder 1000. The decoder 1000 includes a processor 1002, a memory 1004, and a decoding application 1006. The decoding application 1006 may include a computer program or application stored in memory 1004 and containing instructions for configuring the processor 1002 to perform operations such as those described herein. The decoding application 1006 may include an entropy decoder configured to reconstruct residuals based, at least in part, on reconstructing significant-coefficient flags, as described herein. It will be understood that the decoding application 1006 may be stored in on a computer readable medium, such as a compact disc, flash memory device, random access memory, hard drive, etc.

It will be appreciated that the decoder and/or encoder according to the present application may be implemented in a number of computing devices, including, without limitation, servers, suitably programmed general purpose computers, audio/video encoding and playback devices, set-top television boxes, television broadcast equipment, and mobile devices. The decoder or encoder may be implemented by way of software containing instructions for configuring a processor to carry out the functions described herein. The software instructions may be stored on any suitable non-transitory computer-readable memory, including CDs, RAM, ROM, Flash memory, etc.

It will be understood that the encoder described herein and the module, routine, process, thread, or other software component implementing the described method/process for configuring the encoder may be realized using standard computer programming techniques and languages. The present application is not limited to particular processors, computer languages, computer programming conventions, data structures, other such implementation details. Those skilled in the art will recognize that the described processes may be implemented as a part of computer-executable code stored in volatile or non-volatile memory, as part of an application-specific integrated chip (ASIC), etc.

Certain adaptations and modifications of the described embodiments can be made. Therefore, the above discussed embodiments are considered to be illustrative and not restrictive.

What is claimed is:

1. A method of decoding a bitstream of encoded video by reconstructing coefficients for a transform unit, wherein the transform unit is partitioned into a plurality of coefficient groups each containing a respective set of coefficients, and each of the non-zero coefficients having a sign bit indicating whether the coefficient is positive or negative, the method comprising:
    for each coefficient group of the plurality of coefficient groups:
        determining whether to use sign bit hiding to decode a sign bit for a syntax element in the coefficient group based on whether a count of coefficients between a first non-zero coefficient in the coefficient group and a last non-zero coefficient in the coefficient group exceeds a threshold;
        when it is determined that sign bit hiding is to be used for the coefficient group:
            summing an absolute value of the coefficients in the coefficient group, and based on whether the absolute value is even or odd, assigning a sign to-the sign bit for-the syntax element in the coefficient group.

2. The method claimed in claim 1, wherein the syntax element is a sign bit of a coefficient in another coefficient group in the transform unit.

3. The method claimed in claim 1, wherein determining to use sign bit hiding to decode a sign bit for a syntax element in the coefficient group comprises determining to use sign bit hiding when the count of non-zero coefficients in the coefficient group exceeds the threshold.

4. The method claimed in claim 1, wherein determining whether to use sign bit hiding to decode a sign bit for a syntax element in the coefficient group further includes determining whether the sum of the absolute value of the coefficients in that coefficient group exceeds a second threshold value.

5. The method claimed in claim 1, wherein determining to use sign bit hiding for decoding comprises determining that the coefficient group contains at least a threshold number of coefficients within that coefficient group between a first non-zero coefficient in that coefficient group and last non-zero coefficient in that coefficient group, in a scan order within that coefficient group.

6. The method claimed in claim 5, wherein determining to use sign bit hiding for decoding comprises determining that an adjacent coefficient group contains at least one non-zero coefficient, with the adjacent coefficient group comprising either of a coefficient group to the right or a coefficient group below a current coefficient group.

7. A decoder for decoding a bitstream of encoded video by reconstructing coefficients for a transform unit, wherein the transform unit is partitioned into a plurality of coefficient groups each containing a respective set of coefficients, and each of the non-zero coefficients having a sign bit indicating whether the coefficient is positive or negative, the decoder comprising:
   a processor;
   a memory; and a decoding application stored in memory and containing instructions that, when executed, cause the processor to:
   for each coefficient group of the plurality of coefficient groups:
   determine, for a coefficient group in the transform unit, whether to use sign bit hiding to decode a sign bit for a syntax element in the coefficient group based on whether a count of coefficients between a first non-zero coefficient in the coefficient group and a last non-zero coefficient in the coefficient group exceeds a threshold; and
   when it is determined that sign bit hiding is to be used for the coefficient group:
   sum an absolute value of the coefficients in the coefficient group, and
   based on whether the absolute value is even or odd, assign a sign to the sign bit for the syntax element in the coefficient group.

8. The decoder claimed in claim 7, wherein the syntax element is a sign bit of a coefficient in another coefficient group in the transform unit.

9. The decoder claimed in claim 7, wherein determining to use sign bit hiding comprises determining to use sign bit hiding when the count of non-zero coefficients in that coefficient group exceeds the threshold.

10. The decoder claimed in claim 9, wherein the instructions cause the processor to determine to use sign bit hiding by further determining that the sum of the absolute value of the coefficients in the coefficient group exceeds a threshold value.

11. The decoder claimed in claim 7, wherein the instructions cause the processor to determine to use sign bit hiding by determining that the coefficient group contains at least a threshold number of coefficients within that coefficient group between a first non-zero coefficient in that coefficient group and last non-zero coefficient in that coefficient group, in a scan order within that coefficient group.

12. The decoder claimed in claim 11, wherein the instructions cause the processor to determine to use sign bit hiding by determining that an adjacent coefficient group contains at least one non-zero coefficient, with the adjacent coefficient group comprising either of the coefficient group to the right or the coefficient group below a current coefficient group.

13. A non-transitory processor-readable medium storing processor-executable instructions, which, when executed, configures one or more processors to decode a bitstream of encoded video by reconstructing coefficients for a transform unit, wherein the transform unit is partitioned into a plurality of coefficient groups each containing a respective set of coefficients, and each of the non-zero coefficients having a sign bit indicating whether the coefficient is positive or negative, and wherein the instructions further cause the processor to:
   for each coefficient group in the plurality of coefficient groups:
   determine whether to use sign bit hiding to decode a sign bit for a syntax element in the coefficient group based on whether a count of coefficients between a first non-zero coefficient in the coefficient group and a last non-zero coefficient in the coefficient group exceeds a threshold; and
   when it is determined that sign bit hiding is to be used for the coefficient group:
   sum an absolute value of the coefficients in the coefficient group, and
   based on whether the absolute value is even or odd, assign a sign to the sign bit for-the syntax element in the coefficient group.

* * * * *